United States Patent [19]

Louderback et al.

[11] 4,344,864

[45] Aug. 17, 1982

[54] METHOD FOR INCREASING SHELF-LIFE OF A SERUM CONJUGATED BILIRUBIN REFERENCE COMPOSITION AND COMPOSITION PRODUCED THEREBY

[75] Inventors: Allan L. Louderback, Temple City; Thomas J. Foley, Diamond Bar, both of Calif.

[73] Assignee: Beckman Instruments, Inc., Fullerton, Calif.

[21] Appl. No.: 202,269

[22] Filed: Oct. 30, 1980

[51] Int. Cl.$^3$ ............................................... G01N 33/48
[52] U.S. Cl. .................................. 252/408; 23/230 B; 23/905
[58] Field of Search ............... 252/408; 23/230 B, 905

[56] References Cited

U.S. PATENT DOCUMENTS

| | | | |
|---|---|---|---|
| 3,876,375 | 4/1975 | Maurukas | 252/408 |
| 4,189,401 | 2/1980 | Louderback | 252/408 |
| 4,201,694 | 5/1980 | Louderback | 252/408 |
| 4,260,579 | 4/1981 | Barton et al. | 252/408 |
| 4,288,343 | 9/1981 | Louderback | 252/408 |
| 4,311,665 | 1/1982 | Wu | 252/408 |

OTHER PUBLICATIONS

Henry, R. J. et al., Clinical Chemistry, Principles and Techniques, 2nd Ed., Harper Row Publishers, N.Y., pp. 1038-1070 (1974).
Ostrow, J. D., et al., Biochem. J., vol. 120, pp. 311-327 (1970).
Billing, B. H., et al., Biochem. J., vol. 65, pp. 774-784 (1957).
Michaelsson, M., Scand. J. Clin. Lab. Inves., vol. 13, Suppl. 56, pp. 1-80 (1961).
Doumas, B. T., et al., Clin. Chem., vol 19, No. 9, pp. 984-993 (1973).
Louderback, A., et al., Fresenius Z. Anal. Chem., vol. 301, p. 145 (1980).

*Primary Examiner*—Teddy S. Gron
*Attorney, Agent, or Firm*—R. J. Steinmeyer; J. E. Vanderburgh; Robert S. Frieman

[57] ABSTRACT

A stable blood serum conjugated bilirubin reference composition characterized in that the composition possess a pH of from about 8.2 to bout 9.2 and comprises (a) a sulfhydryl compound in an amount sufficient to enhance the stability of the conjugated bilirubin and (b) a chelating agent in an amount sufficient to bind all the metals present in the blood serum moiety of the composition. This blood serum conjugated bilirubin composition when stored in a gas impervious vial under an inert atmosphere has an excellent shelf life.

20 Claims, No Drawings

METHOD FOR INCREASING SHELF-LIFE OF A SERUM CONJUGATED BILIRUBIN REFERENCE COMPOSITION AND COMPOSITION PRODUCED THEREBY

BACKGROUND OF THE INVENTION

1. Field of the Invention

This invention relates to a laboratory material and, more particularly, to a stable blood serum conjugated bilirubin reference composition.

2. Description of the Prior Art

The relationships among bilirubin, its glucuronides, and the azo pigments are set forth in FIG. 22-3 of Henry et al., *Clinical Chemistry, Principles and Technics*, 2nd Edition, Harper & Row, New York, N.Y. (1974), p. 1040 (1). Bilirubin is also referred to in the art as either "unconjugated bilirubin" or "indirect bilirubin." In contrast, bilirubin monoglucuronide and bilirubin diglucuronide are referred to in the art as either "conjugated bilirubin" or "direct bilirubin." "Total bilirubin" is the sum of the unconjugated bilirubin and conjugated bilirubin present in the assayed sample.

The measurement of conjugated and unconjugated bilirubin levels in a patient's serum is necessary in order to diagnose various possible causes of hyperbilirubinemia. To assure the accuracy of such measurements, it is highly desirable to have stable reference compositions that can be employed either as a reference standard or as a reference control, i.e., to either calibrate an instrument or to periodically verify that the instrument is still operating within the tolerances desired, respectively.

Although there is literature suggesting ways to stabilize unconjugated bilirubin (2) and azobilirubin (3–5), literature with respect to the stabilization of conjugated bilirubin appears to be sparse (6). Furthermore, the only commercial reference composition containing a form of conjugated bilirubin is a lyophilized product which has a reconstituted shelf life of only 3 days when stored between 2°–8° C. (10).

Accordingly, it would be highly desirable to have a stable conjugated bilirubin reference composition. This stable conjugated bilirubin reference composition would be useful as both a control and a standard to assure the accuracy of clinical assays and thereby help to improve the accuracy of the diagnosis based upon such data.

SUMMARY OF THE INVENTION

In accordance with the present invention, there is provided a stable conjugated bilirubin reference composition which possesses a proven shelf life in excess of 1 year when stored at +4° C.

More particularly, this invention encompasses a blood serum conjugated bilirubin reference composition characterized in that the composition possesses a pH of about 8.2 to about 9.2 and further comprises (a) a sulfhydryl compound in an amount sufficient to enhance the stability of conjugated bilirubin and (b) a chelating agent in an amount sufficient to bind all the metals present in the blood serum moiety of the composition. Furthermore, it is desirable to store the blood serum reference composition of the present invention in a gas impervious container and, preferably, also under an inert atmosphere.

DESCRIPTION OF THE PREFERRED EMBODIMENTS

The improved blood serum reference composition of the instant invention is of the type comprising blood serum having a conjugated bilirubin constituent of a known value. In accordance with the invention, the improved blood serum reference composition is characterized in that the composition possesses a pH of from about 8.2 to about 9.2, preferably, from about 8.4 to about 8.9, and more preferably about 8.7.

The pH can be adjusted by any conventional means employed by those skilled in the art, e.g., by the addition of NaOH to the composition.

This invention's improved blood serum reference composition is also characterized in that the composition further comprises a sulfhydryl compound in an amount sufficient to further enhance the stability of conjugated bilirubin.

The normal range of oxidation-reduction (REDOX) potential for plasma is from about +7 to about +40 millivolts depending upon the freshness of the plasma. It has been discovered that by reducing the REDOX potential of plasma with sulfhydryl compounds, one is able to greatly prolong the shelf life of a conjugated bilirubin composition. Although the exact amount of the sulfhydryl compound employed is not critical, one should avoid using too much sulfhydryl compound in order to avoid cross linking the sulfhydryl bonds. The cross-linking of sulfhydryl bonds forms a disulfide bridge (—S—S—) which results in a polymer matrix. This polymer matrix imparts a gel-like consistency to the composition thereby rendering it undesirable for clinical use. In a similar fashion, if too little sulfhydryl compound is employed, the conjugated bilirubin composition will not be stable. Therefore, sulfhydryl compounds should be employed in an amount sufficient to enhance the stability of conjugated bilirubin without imparting undesirable characteristics to the composition, said amount preferably being sufficient to reduce the REDOX potential of the composition to from about −30 to about −300 millivolts. More preferably the sulfhydryl compounds are employed in an amount sufficient to reduce the REDOX potential to from about −100 to about −200 millivolts. Optimally the amount of sulfhydryl compounds employed is such that the REDOX potential is reduced to about −160 millivolts.

Any of the numerous sulfhydryl compounds known to those skilled in the art can be employed as a reducing agent in the instant invention. For example, the sulfhydryl compound can be selected from a group consisting of dithioerythreitol, dithiothretitol (DTE), mercaptoethanol, cysteine, reduced gluthathione, N-acetyl cysteine, mercaptoacetate, as well as mixtures thereof. Preferably, the sulfhydryl compound is DTE.

In addition to the above, this invention's improved blood serum reference composition is also further characterized in that the composition further comprises a chelating agent in an amount sufficient to bind all the metals present in the blood serum moiety of the composition. Although the exact amount of chelating agent employed is not critical, from about 25 to about 1,000, preferably from about 5 to about 150, and more preferably about 100 mg of chelating agent is used per 100 ml of blood serum reference composition of the instant invention.

Essentially any chelating agent can be used in the composition of the present invention. Known chelating agents are discussed in Flaschka et al., Chelates in Analytical Chemistry, Volumes I–V, Marcel Decker, Inc., New York, N.Y., said publication being incorporated herein in toto by reference. Typical chelating agents include ethylenediaminetetraacetic acid (EDTA), nitrolotriacetic acid, ethylenediamino, diethylenetriamine, triethyltetramine, tetraethylenepentamine, pentaethylenehexamine, N-hydroxyethyliminodiacetic acid, N-hydroxyethyl-N,N',N', ethylenediaminitriacetic acid, N,N,N'N'',N''-diethylenetriaminepentaacetic acid, citric acid, tartaric acid, gluconic acid, tripolyphosphate ion, polyphosphate anion, N,N'-ethylenebis[2-o-hydroxyphenyl] glycine, 3,5-disulfopyrocatechol, bis(othohydroxybenzyl)ethylenediamine-N,N'-diacetic acid, salts thereof, and mixtures thereof. Preferably the chelating agent is selected from the group consisting of EDTA, salts thereof and mixtures. More preferably, the chelating agent is EDTA disodium salt. Other salts of EDTA include the sodium potassium salt and the tetrasodium salt thereof.

Although the blood serum reference composition of the type comprising blood serum having a conjugated bilirubin constituent of a known value can be employed in the present invention, it is preferred to employ a conjugated bilirubin reference composition comprising in its non-biological component from about 60 to about 80, more preferably from about 66 to about 70, weight percent water, from about 20 to about 40, more preferably from about 30 to about 34, weight percent of at least one alkylene polyol having from 2–5 carbon atoms, the remainder being conjugated bilirubin and, optionally, other natural biological materials selected from a group consisting of unconjugated bilirubin, blood serum, enzymes, metabolites, electrolytes, and hormones. This matrix is described in detail in U.S. Pat. No. 3,876,375, said publication being incorporated herein in toto by reference.

The blood serum reference composition of the present invention preferably is stored in a gas impervious container, such as a glass ampule, under an inert gas atmosphere, such as nitrogen, argon, or helium. Preferably, the container is also impervious to visible light.

The conjugated bilirubin employed in the blood serum reference composition of this invention can be either isolated from natural sources via techniques well known to those skilled in the art (6) or can be in the form of similar synthetically substituted bilirubin derivatives made via techniques well known to those skilled in the art (7–9).

Conjugated bilirubin obtained from natural sources include monoglucuronide bilirubin and diglucuronide bilirubin. Synthetically substituted bilirubin derivatives similar to conjugated bilirubin include, but are not limited to, ditaurobilirubin, monotaurobilirubin, monoglycine bilirubin, and diglycine bilirubin. The preferred form of conjugated bilirubin employed in the instant invention is selected from a group consisting of ditaurobilirubin, monotaurobilirubin, and mixtures thereof. Optimally, ditaurobilirubin is employed in the reference composition of this invention. (Ditaurobilirubin is commercially available from Porphyrin Products, Logan, Utah.)

The stable blood serum conjugated bilirubin reference composition of the instant invention can be employed as a blood serum conjugated bilirubin reference standard or as a blood serum conjugated bilirubin reference control, i.e., the composition can be employed to either calibrate an instrument or can be employed to periodically verify that the instrument is still operating within the tolerances desired. For the above uses, the blood serum conjugated bilirubin reference composition of the instant invention can contain known amounts of conjugated bilirubin up to about 20 milligrams per deciliter (mg/dl). Other ranges of conjugated bilirubin of use to the clinical chemist include ranges from about 0.1 to about 20 mg/dl and also from about 0.1 to about 10 mg/dl.

The following examples are provided for the purpose of further illustration only and are not intended to be limitations on the disclosed invention.

EXAMPLE 1

Conjugated bilirubin serum reference compositions containing the constituents set forth in Table I were prepared. The compositions were placed in amber ampules (each ampule containing 1.3 ml of a particular composition) and sealed with an inert gas ($N_2$) overlay. Some of the ampules were stored at −22° C. while others were stored at +4° C. Periodically, some of the vials were removed from their storage environment and assayed via the following protocol:

I. Method: Jendrassik-Grof

A. Reagents
1. Caffeine (37.5 g/l), Na-benzoate (56 g/l), Na-Acetate (anhydrous, 56 g/l)
2. Sulfanilic Acid: 5 g/l in 0.18 mol/l HCl
3. Na-nitrite: 5 g/l in deionized water
4. Diazo Reagent (DSA): 10 ml Reagent 2 + 0.5 ml Reagent 3
5. Alkaline Tartrate: NaOH (75 g/l) + K-Na-tartrate (323 g/l)

B. Total Bilirubin (Total Volume of Reactants = 5.3 ml)
2.0 ml Caffeine Reagent
0.2 ml Sample
0.5 ml DSA
Incubate at room temperature for 10 minutes
0.1 ml 2% Ascorbic Acid
1.0 ml 0.05 N NCl
1.5 ml Alkaline Tartrate C. Direct Bilirubin (Total Volume of Reactants = 5.3 ml)
1.0 ml 0.05 N HCl
0.2 ml Sample
0.5 ml DSA
Incubate at room temperature for 10 minutes
0.1 ml 2% Ascorbic Acid
2.0 ml 0.05 N HCl
1.5 ml Alkaline Tartrate The samples were assayed at 600 nm and the data obtained therefrom are set forth in Table II.

TABLE I

| Ingredient | Low Level | High Level |
|---|---|---|
| Water, 66⅔ weight % | X | X |
| Ethylene glycol, 33⅓ weight % | X | X |
| DTE, 15 mg/dl | X | X |
| EDTA, disodium salt, 100 mg/dl | X | X |
| Conjugated bilirubin* | ~4.0 mg/dl pH 8.7 | ~8.0 mg/dl pH 8.7 |

*Consists primarily of ditaurobilirubin.

TABLE II

| | Low Level | | | | | | | |
|---|---|---|---|---|---|---|---|---|
| | Total −22° C. | | Direct +4° C. | | Total −22° C. | | Direct +4° C. | |
| Day | mg/dl | % Δ[1] | mg/dl | % Δ | mg/dl | % Δ | mg/dl | % Δ |
| 1 | 3.15 | N/A[2] | 3.14 | N/A | T/E[3] | U[4] | T/E | U |
| 81 | 3.11 | −1.27% | 3.07 | −2.23% | 2.42 | N/A | 2.46 | N/A |
| 183 | 3.08 | −2.22% | 3.02 | −3.82% | 2.44 | 0.83% | 2.36 | −4.07% |
| 239 | 3.18 | 0.95% | 3.13 | −0.32% | 2.51 | 3.72% | 2.55 | 3.67% |
| 339 | 3.18 | 0.95% | 3.14 | 0 | 2.47 | 2.07% | 2.45 | −0.41% |

[1] % Δ denotes percent change from first assay value.
[2] N/A denotes not applicable.
[3] T/E denotes technical error.
[4] U denotes unavailable due to T/E.

The mg/dl values set forth in Table II indicate the total bilirubin and direct bilirubin values obtained via the particular assay technique employed in Example 1. The total bilirubin and direct bilirubin values obtained did not vary more than ±4.65% from the first assay thereof (i.e., from day 1 for total bilirubin and from day 81 for direct bilirubin) for a period of up to 339 days. This minute degree of variation can be attributed to the slight difference normally observed between consecutive assays. Accordingly, the data set forth in Table II demonstrates that serum conjugated bilirubin reference compositions within the scope of the instant invention are stable for periods of time far exceeding the shelf life of prior art serum conjugated bilirubin reference compositions.

Based on this disclosure, many other modifications and ramifications will naturally suggest themselves to those skilled in the art. These are intended to be comprehended as within the scope of this invention.

BIBLIOGRAPHY

1. Henry et al., *Clinical Chemistry, Principles and Technics*, 2nd Edition, Harper Row, New York, N.Y. (1974) p. 1040.
2. Michaelsson, *The Scandinavian Journal of Clinical & Laboratory Investigation*, 13(Supplementum 56):62–63.
3. Michaelsson, *The Scandinavian Journal of Clinical & Laboratory Investigation*, 13(Supplementum 56):55–57.
4. Holtz et al., *Clin. Chem. Acta*, 20:355–357 (1968).
5. Doumas et al., *Clin. Chem.*, 19(9) 984–993 (1973).
6. Ostrow et al., *Biochem. J.* 120:311–327 (1970).
7. Jirsa et al., *Nature*, 177(4515):895 (1956).
8. Chem. Abstracts:15621(i) (1958).
9. Chem. Abstracts:15622(b) (1958).
10. Hyland Diagnostics, Division of Travenol Laboratories, Elevated Bilirubin Control, Direction Insert 00-35-09-900AA (1979).

The embodiments of the invention in which an exclusive property or privilege is claimed are defined as follows:

1. An improved blood serum reference composition of the type comprising blood serum having a conjugated bilirubin constitutent of known value, characterized in that said composition possesses a pH of from about 8.2 to about 9.2 and further comprises:
   (a) a sulfhydryl compound in an amount sufficient to further enhance the stability of conjugated bilirubin and
   (b) a chelating agent in an amount sufficient to bind the metals present in said blood serum.

2. The composition of claim 1 wherein said sulfhydryl compound is present in an amount such that the oxidation-reduction potential of said composition is from about −30 to about −300 millivolts and wherein said composition comprises from about 25 to about 1,000 mg chelating agent per 100 ml serum.

3. The composition of claim 1 wherein said sulfhydryl compound is present in an amount such that the oxidation-reduction potential of said composition is from about −100 to about −200 millivolts, wherein said composition comprises from about 50 to about 150 mg chelating agent per 100 ml serum, and wherein said composition possesses a pH of from about 8.4 to about 8.9.

4. The composition of claim 3 wherein said sulfhydryl compound is present in an amount such that the oxidation-reduction potential of said composition is about −160 millivolts, wherein said composition comprises about 100 mg chelating agent per 100 ml serum, and wherein said composition possesses a pH of about 8.7.

5. The composition of claim 4 wherein said sulfhydryl compound is selected from a group consisting of dithioerythreitol, dithiothreitol, mercaptrethanol, cysteine, reduced gluthione, N-acetyl cysteine, mercaptoacetate, and mixtures thereof, and wherein said chelating agent is selected from a group consisting of ethylenediaminetetraacetic acid, nitrilotriacetic acid, ethylenediamino, diethylenetriamine, triethyltetramine, tetraethylenepentamine, pentaethylenehexamine, N-hydroxyethyliminodiacetic acid, N-hydroxyethyl-N,N',N',-ethylenediaminitriacetic acid, N,N,N',N'',N''-diethylenetriaminepentaacetic acid, citric acid, tartaric acid, gluconic acid, tripolyphosphate ion, polyphosphate anion, N,N'-ethylenebis[2-(o-hydroxyphenyl]glycine, 3,5-disulfopyrocatechol, bis-(othohydroxybenzyl)ethylenediamine-N,N'-diacetic acid, salts thereof, and mixtures thereof.

6. The composition of claim 5 wherein said sulfhydryl compound is dithiothreitol and wherein said chelating agent is selected from the group consisting of ethylenediaminetetraacetic acid, salts thereof, and mixtures thereof.

7. An improved bilirubin reference composition comprising in its non-biological component from about 60 to about 80 weight percent water, from about 20 to about 40 weight percent of at least one alkylene polyol having from 2 to 5 carbon atoms, the remainder being conjugated bilirubin and, optionally, other natural biological materials selected from a group consisting of unconjugated bilirubin, blood serum, enzymes, metabolites, electrolytes, and hormones, characterized in that said composition possesses a pH of from about 8.2 to about 9.2 and further comprises:
   (a) a sulfhydryl compound in an amount sufficient to further enhance the stability of conjugated bilirubin and (b) a chelating agent in an amount sufficient to bind the metals present in said blood serum.

8. The composition of claim 7 wherein said sulfhydryl compound is present in an amount such that the oxidation-reduction potential of said composition is from about −30 to about −300 millivolts and wherein said composition comprises from about 25 to about 1,000 mg chelating agent per 100 ml serum.

9. The composition of claim 7 wherein said sulfhydryl compound is present in an amount such that the oxidation-reduction potential of said composition is from about −100 to about −200 millivolts, wherein said composition comprises from about 50 to about 150 mg chelating agent per 100 ml serum, and wherein said composition possesses a pH of from about 8.4 to about 8.9.

10. The composition of claim 9 wherein said sulfhydryl compound is present in an amount such that the oxidation-reduction potential of said composition is about −160 millivolts, wherein said composition comprises about 100 mg chelating agent per 100 ml serum, and wherein said composition possesses a pH of about 8.7.

11. The composition of claim 10 wherein said sulfhydryl compound is selected from a group consisting of dithioerythreitol, dithiothreitol, mercaptrethanol, cysteine, reduced gluthione, N-acetyl cysteine, mercaptoacetate, and mixtures thereof, and wherein said chelating agent is selected from a group consisting of ethylenediaminetetraacetic acid, nitrilotriacetic acid, ethylenediamino, diethylenetriamine, triethyltetramine, tetraethylenepentamine, pentaethylenehexamine, N-hydroxyethyliminodiacetic acid, N-hydroxyethyl-N,N',N',-ethylenediamietriacetic acid, N,N,N',N'',N'''-diethylenetriaminepentaacetic acid, citric acid, tartaric acid, gluconic acid, tripolyphosphate ion, polyphosphate anion, N,N'-ethylenebis[2-(o-hydroxyphenyl]glucine, 3,5-disulfopyrocatechol, bis-othohydroxybenzyl-)ethylenediamine-N,N'-diacetic acid, salts thereof, and mixtures thereof.

12. The composition of claim 7 wherein said sulfhydryl compound is dithiothreitol and wherein said chelating agent is selected from the group consisting of ethylenediaminetetraacetic acid, salts thereof, and mixtures thereof.

13. The composition of any one of claims 1-11 or 12 wherein said conjugated bilirubin is selected from a group consisting of monoglucuronide bilirubin, diglucuronide bilirubin, monotauratobilirubin, ditauratobilirubin, monoglycine bilirubin, diglycine bilirubin, and mixtures thereof.

14. The composition of any one of claims 1-11 or 12 wherein said conjugated bilirubin is ditauratobilirubin.

15. An article comprising a gas impervious container having located therein an inert gas and the composition of any one of claims 1-11 or 12.

16. An article comprising a gas impervious container which is also impervious to visible light and having located therein an inert gas and the composition of any one of claims 1-11 or 12.

17. An article comprising a gas impervious container having located therein an inert gas and the composition of any one of claims 1-11 or 12 wherein said conjugated bilirubin is selected from a group consisting of monoglucuronide bilirubin, diglucuronide bilirubin, monotauratobilirubin, ditauratobilirubin, monoglycine bilirubin, diglycine bilirubin, and mixtures thereof.

18. An article comprising a gas impervious container having located therein an inert gas and the composition of any one of claims 1-11 or 12 wherein said conjugated bilirubin is ditauratobilirubin.

19. An article comprising a gas impervious container which is also impervious to visible light and having located therein an inert gas and the composition of any one of claims 1-11 or 12 wherein said conjugated bilirubin is selected from a group consisting of monoglucuronide bilirubin, diglucuronide bilirubin, monotauratobilirubin, ditauratobilirubin, monoglycine bilirubin, diglycine bilirubin, and mixtures thereof.

20. An article comprising a gas impervious container which is also impervious to visible light and having located therein an inert gas and the composition of any one of claims 1-11 or 12 wherein said conjugated bilirubin is ditauratobilirubin.

* * * * *